United States Patent
Bifone et al.

(10) Patent No.: US 9,365,420 B2
(45) Date of Patent: Jun. 14, 2016

(54) THREE-DIMENSIONAL DISPERSIBLE NANORESONATOR STRUCTURE FOR BIOLOGICAL, MEDICAL AND ENVIRONMENTAL APPLICATIONS AND METHOD FOR MANUFACTURE THEREOF

(71) Applicants: FONDAZIONE INSTITUTO ITALIANO DI TECNOLOGIA, Genoa (IT); SCUOLA SUPERIORE DI STUDI UNIVERSITARI E DI PERFEZIONAMENTO SANT'ANNA, Pisa (IT); SCUOLA NORMALE SUPERIORE, Pisa (IT)

(72) Inventors: Angelo Bifone, Verona (IT); Vito Clerico', Pisa (IT); Alessandro Tredicucci, Pisa (IT); Pasqualantonio Pingue, Pisa (IT); Adriano Boni, Lucca (IT); Fabio Recchia, Bari (IT)

(73) Assignees: FONDAZIONE ISTITUTO ITALIANO DI TECNOLOGIA, Genoa (IT); SCUOLA SUPERIORE DI STUDI UNIVERSITARI E DI PERFEZIONAMENTO SANT'ANNA, Pisa (IT); SCUOLA NORMALE SUPERIORE, Pisa (IT)

( * ) Notice: Subject to any disclaimer, the term of this patent is extended or adjusted under 35 U.S.C. 154(b) by 0 days.

(21) Appl. No.: 14/655,620
(22) PCT Filed: Dec. 31, 2013
(86) PCT No.: PCT/IB2013/061433
§ 371 (c)(1),
(2) Date: Jun. 25, 2015
(87) PCT Pub. No.: WO2014/106808
PCT Pub. Date: Jul. 10, 2014

(65) Prior Publication Data
US 2015/0338341 A1 Nov. 26, 2015

(30) Foreign Application Priority Data
Jan. 2, 2013 (IT) .................................. TO13A0001

(51) Int. Cl.
*G01J 5/00* (2006.01)
*B82Y 30/00* (2011.01)
*G01N 29/036* (2006.01)
*G01N 29/24* (2006.01)
*G01N 21/3581* (2014.01)

(52) U.S. Cl.
CPC ............ *B82Y 30/00* (2013.01); *G01N 21/3581* (2013.01); *G01N 29/036* (2013.01);
(Continued)

(58) Field of Classification Search
CPC .......... G01N 21/3581; G01N 29/2418; G01N 29/036; G01N 2291/02466
USPC ....................................................... 250/338.1
See application file for complete search history.

(56) References Cited

U.S. PATENT DOCUMENTS

2003/0166297 A1    9/2003  Natan

FOREIGN PATENT DOCUMENTS

WO    WO 2011/050272 A2    4/2011

OTHER PUBLICATIONS

Clerico et al. "Water-dispersible Three-dimensional LC-nanoresonators", PLOS ONE, vol. 9, Issue 8. Aug. 2014.*
(Continued)

*Primary Examiner* — David Porta
*Assistant Examiner* — Meenakshi Sahu
(74) *Attorney, Agent, or Firm* — Merchant & Gould P.C.

(57) ABSTRACT

A three-dimensional nanoresonator structure has a stack of laterally confined layers including at least a first layer and a second layer of different conductive materials between which a dielectric layer is interposed. The layers have at least a respective accessible surface area exposed to an environment in which the structure is immersed. Multiple three-dimensional nanoresonators that can be dispersed in an environment are formed from an array of nanoresonators fixed to a sacrificial substrate. The nanoresonators are subsequently separated from the substrate and conjugated with a chemical agent adapted to promote the formation of a stable colloidal suspension of nanoresonators in a liquid medium.

15 Claims, 8 Drawing Sheets

(52) U.S. Cl.
CPC .... *G01N29/2418* (2013.01); *G01N 2291/0255* (2013.01); *G01N 2291/0257* (2013.01); *G01N 2291/02466* (2013.01)

(56) References Cited

OTHER PUBLICATIONS

International Search Report for corresponding International Patent Application No. PCT/IB2013/061433 May 9, 2014.

Su, K. et al., "Tunable and augmented plasmon resonances of Au/SiO$_2$/Au nanodisks", *Applied Physics Letters*, 88(6): 63118-1-63118-3 (2006).

Wu, D. et al., "Tunable near-infrared optical properties of three-layered gold-silica-gold nanoparticles", *Applied Physics B*, 97(1): 193-197 (2009).

Joshi, B. et al., "Numerical Studies of Metal-Dielectric-Metal Nanoantennas", *IEEE Transactions of Nanotechnology*, 9(6): 701-707 (2010).

Kudelski, A., et al., "Silica-Covered Silver and Gold Nanoresonators for Raman Analysis of Surfaces of Various Materials", *J. Phys. Chem. C*, 116: 16167-16174 (2012).

Nagel, M. et al., "A functionalized THz sensor for marker-free DNA analysis", *Phys. Med. Biol.*, 48: 3625-3636 (2003).

\* cited by examiner

THREE-DIMENSIONAL DISPERSIBLE NANORESONATOR STRUCTURE FOR BIOLOGICAL, MEDICAL AND ENVIRONMENTAL APPLICATIONS AND METHOD FOR MANUFACTURE THEREOF

This application is a National Stage Application of PCT/IB2013/061433, filed 31 Dec. 2013, which claims benefit of TO2013A000001, filed 2 Jan. 2013 in Italy and which applications are incorporated herein by reference. To the extent appropriate, a claim of priority is made to each of the above disclosed applications.

BACKGROUND OF THE INVENTION

The present invention relates to nanosensors, in particular nanosensors for biological, medical and environmental applications, and more specifically a three-dimensional nanoresonator structure.

The invention also relates to a method for the manufacture, by lithographic techniques, of three-dimensional nanoresonators that are dispersible in a liquid such as water.

Nanoresonators, also known as nanoantennas, are resonator devices of nanometric dimensions which, when exposed to wide-spectrum exciting electromagnetic radiation, show increased absorption at a natural resonant frequency determined by the characteristics of the resonator structure and/or by the interactions with the environment in which they are immersed, this frequency being located between the THz range and the near infrared wavelengths.

Two classes of nanoresonators, namely structured nanoresonators and nanoparticles with resonant properties, are known in the prior art.

Structured nanoresonators may be described as nanometric-scale circuits, the resonant properties of which are determined by the inductance and capacitance characteristics of the circuit, and are therefore also known as LC metamaterials.

Metamaterials have characteristic properties which depend on the geometry of the device, instead of on its chemical composition.

Figure 1:
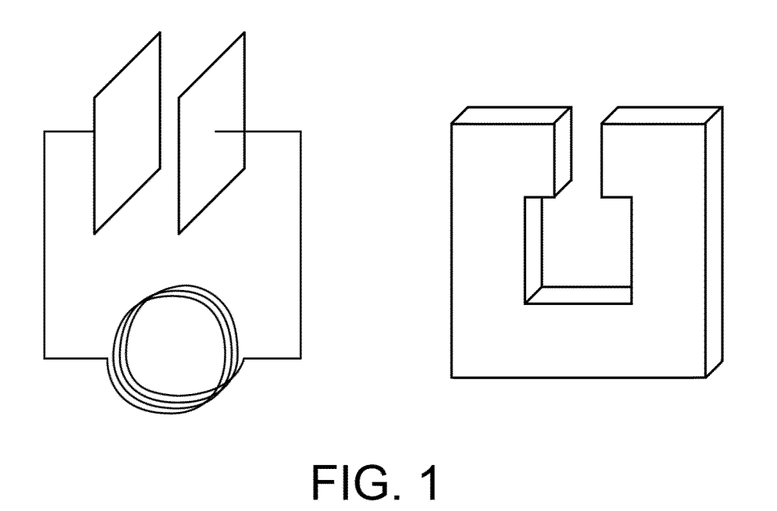
FIG. 1 shows a two-dimensional nanoresonator configuration according to the prior art, already discussed in the introductory part of this description.

The most common structured nanoresonators are based on a two-dimensional open-loop configuration, such as that shown in FIG. 1 together with an equivalent electrical circuit.

This two-dimensional nanoresonator structure comprises a conductive metal microstrip (typically made of gold) shaped to form an open loop, in which, at the operating frequencies of the device, the loop-shaped path shows distributed inductive behaviour and the gap in the ring acts as a capacitor. The corresponding values of capacitance and inductance depend on the geometrical parameters of the microstrip, and the resonant frequency $f=1/\sqrt{LC}$ can easily be tuned by modifying the dimensional parameters of the circuit during the design process.

Nanoresonators of this type have an intrinsically two-dimensional structure, which has to be supported on the surface of a substrate from which, therefore, they cannot be separated. There is a known method in the prior art for making arrays of nanoresonators anchored to a substrate by using a lithographic procedure for the versatile configuration of at least one layer of material deposited on the substrate by planar deposition techniques.

The resonance of these devices can be tuned over a wide range of wavelengths, by suitable design of the resonance structure, but their use is limited by the dimensions of the array and by the nature of the substrate to which they are anchored.

WO 2011/050272 describes an array of two-dimensional nanoantennas and processes for the efficient manufacture of an array of nanoantennas whose shape is controlled by nanostencil lithography. This method can be used to produce nanoresonator structures on virtually any type of support, whether conductive, non-conductive or magnetic, with properties of flexibility and stretchability if required. The array of nanoantennas formed in this way can be used in spectrometry, for the detection of bioanalytes or inorganic chemical substances having resonant frequencies in the infrared range.

The paper by M. Nagel, F. Richter, P. Haring-Bolivar and H. Kurz, entitled "A functionalized THz sensor for marker-free DNA analysis", published in Phys. Med. Biol., 2003, 403625-3636, describes a functionalized biochip for conducting DNA hybridization experiments. The circuit includes an array of resonators operating at THz frequencies, each comprising a first metal electrode anchored to a substrate, an intermediate non-conductive polymer layer, and a second conductive metal electrode for functionalization, adapted to bind DNA strands. These resonators are used to detect the presence of molecules which bind to the functionalized surface, making use of the fact that their resonance properties vary as a function of the presence of these molecular bonds.

These devices are typically used for in vitro biological analysis, in analyte assays for example, but have the disadvantage that they cannot be injected into a living organism and traced in vivo, because they cannot be separated from the substrate.

Unlike structured nanoresonators, some free metallic nanoparticles, which can be produced by chemical synthesis, are known to act as nanoresonators because of the resonance of the plasmon waves which are established on the surfaces of the molecules.

For example, nanoparticles of $Ag:SiO_2$ and $Au:SiO_2$ in colloidal suspension have been used as electromagnetic nanoresonators, as described by A. Kudelski and S. Wojtysiak, in "Silica-Covered Silver and Gold Nanoresonators for Raman Analysis of Surfaces of Various Materials", published in J. Phys. Chem. C. 2012, 116 (30), pages 16167-16174.

As a general rule, resonant nanoparticles, not bound to any substrate, can be dispersed freely in a fluid medium and can be used advantageously for in vivo applications, by exploiting, where appropriate, their capacity to bind to molecular species present in the fluid medium, which affect their resonance properties.

Unfortunately, however, the resonance properties are mainly determined by the intrinsic characteristics of the material of the nanoparticles, and since the chemical synthesis process does not enable complexes of nanoparticles to be produced with controlled shapes, the resonance can only be tuned over a limited range of wavelengths.

K. H. Su et al., in "Tunable and augmented plasmon resonances of $Au/SiO_2/Au$ nanodisks", published in Applied Physics Letters, vol. 88, no. 6, 10 Feb. 2006, describe three-dimensional resonant nanostructures (nanodiscs) anchored to the original substrate, manufactured by a top-down procedure based on an EBL (Electron Beam Lithography) process on a quartz substrate, on which a first conductive gold layer, an intermediate dielectric layer of $SiO_2$ and a second conductive gold layer are deposited in succession by evaporation. A standard lift-off process defines the three-dimensional structure of the nanodiscs without their material separation from the substrate.

D. J. Wu et al., in "Tunable near-infrared optical properties of three-layered gold-silica-gold nanoparticles", published in Applied Physics B, vol. 97, no. 1, 3 Mar. 2009, provide a theoretical description of plasmon resonance in nanospheres with layers of gold, silica and gold.

Bhuwan Joshi et al., in "Numerical Studies of Metal-Dielectric-Metal Nanoantennas", published in IEEE Transactions on Nanotechnology, vol. 9, no. 6, 6 Nov. 2010, present a theoretical study of cubic and cylindrical nanoantennas formed with two conductive layers separated by an intermediate dielectric layer.

SUMMARY OF THE INVENTION

The object of the present invention is to provide three-dimensional nanoresonators which are free, that is to say not fixed to any substrate and dispersible in a fluid medium, and have resonance properties tunable over a wide spectrum of wavelengths as a result of the design of the resonant structure, while being sensitive to the chemical and physical characteristics of their environment or to the presence of specific molecular species.

The invention also proposes a method for the manufacture of three-dimensional nanoresonators as claimed.

Specific embodiments are described in the dependent claims, the content of which is to be considered as an integral part of the present description.

Briefly, the present invention is based on a technique of manufacturing three-dimensional nanoresonators by a lithographic procedure in which an array of nanoresonators is designed and manufactured on a substrate and the individual nanoresonators are subsequently released from the substrate, and subjected to chemical modification if necessary, for the functionalization of at least one accessible surface exposed to environmental interactions.

The nanoresonators proposed by the invention have an overall layered three-dimensional structure, with layers of different materials, the shape and size of which can be controlled in the design process.

Advantageously, the innovative three-dimensional structure of nanoresonators that can be produced by the method proposed by the invention has a plurality of accessible surfaces, that is to say surfaces exposed to the environment, made of different materials suitable for separate functionalization, thus enhancing the sensing functions of the device.

The functionalization may be such that it allows a free dispersion of the nanoresonators in water or other fluid media, and makes it possible to produce probes sensitive to predetermined molecular interactions, or it may be such that it creates affinities for specific tissues, cells or materials to be analysed.

The nanoresonators produced according to the present invention have characteristics which significantly extend their range of applications, by combining the properties of design flexibility of the resonant frequency over a wide electromagnetic spectrum, typical of prior art two-dimensional nanoreonators, with the dispersibility properties of resonant nanoparticles.

The possibility of tuning the optical properties of these nanoresonators over a wide spectrum of wavelengths, from the visible to the THz region, enables these devices to be adapted to specific applications. Nanoresonators operating in the near infrared region can be used for diagnostic applications on living creatures, since the absorption of the tissues in this spectral range is fairly low (the "biological window"), while nanoresonators operating at THz frequencies can be used to study materials transparent in this region of the electromagnetic spectrum, for example some polymers such as polymethylpentene, polypropylene or polyethylene.

The intrinsically three-dimensional structure of the nanoresonator proposed by the invention has considerable advantages over a two-dimensional nanoresonator structure. This is because the compact three-dimensional structure is capable of being freely self-supporting, with no support by a substrate, without any appreciable changes in its shape and resonant frequency, as a result of which the nanoresonator proposed by the invention is dispersible in solution and is adapted to show stable behaviour based on the controlled design of its intrinsic resonant frequency.

At the same time, because of the possibility of diffusing a plurality of nanoresonators according to the invention in a fluid, the nanoresonators can be injected into a living organism for in vivo analysis as a diagnostic means, or for detecting physiological or biochemical events, or for use in fluid or microfluid assays in which the fluid medium of immersion affects the overall dielectric constant of the resonant circuit, or for impregnating porous materials such as marble or stone used for works of art in investigative and diagnostic operations conducted on cultural assets. Nanoresonators suspended in a liquid phase can also be conjugated with functional groups to bind to specific tissues or cells to be analysed.

BRIEF DESCRIPTION OF THE DRAWINGS

Further characteristics and advantages of the invention will be disclosed more fully in the following detailed description of an embodiment of the invention, provided by way of non-limiting example, with reference to the attached drawings, in which.

DETAILED DESCRIPTION OF THE PREFERRED EMBODIMENTS

Figure 2A:
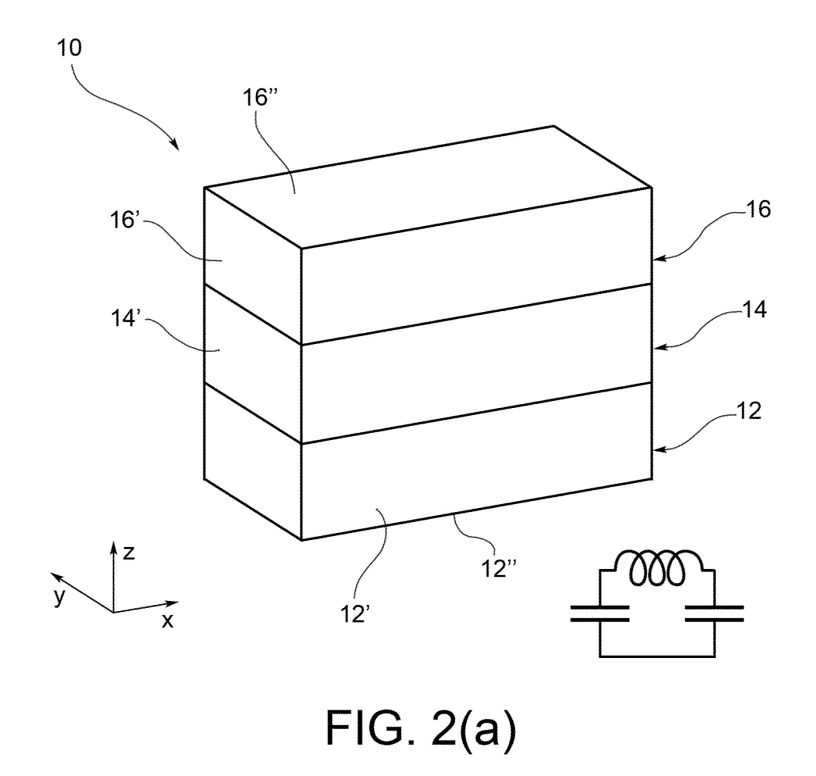
FIGS. 2a-2c are representations of a three-dimensional nanoresonator proposed by the invention, showing (a) the geometrical structure and an equivalent electrical circuit, (b) the pattern of lines of intensity of the electric field in the plane xy, and (c) the pattern of lines of intensity of the magnetic field in the plane xy.

FIG. 2a shows an exemplary structure of a three-dimensional nanoresonator structure according to the invention, indicated as a whole by 10.

The nanoresonator 10 has a generally prismatic structure and comprises a stack of superimposed layers of uniform dimensions, these layers being, respectively, a first electrode layer 12 of conductive material, preferably made of metal and even more preferably made of aluminium, an intermediate layer 14 of dielectric material, preferably an aluminium oxide, and a second electrode layer 16 of conductive material, preferably made of metal and different from the conductive material of the first electrode layer, and even more preferably made of gold.

The shape of this structure is given purely for guidance and other different shapes could be devised without departing from the scope of the present invention. For example, it is possible to make nanoresonators of prismatic shape, having a polygonal or circular cross section, or of any arbitrarily chosen shape; or it is possible to make stacked structures in which the transverse extension and depth of each layer are different from those of the other layers, each of these dimensions and materials contributing to the design of the resonant frequency of the overall structure.

Additionally, nanoresonator structures comprising more than three layers are possible, while it is also possible to make structures containing connection elements (shunts) between non-adjacent conductive layers, so that the electromagnetic resonance properties of the nanoresonator can be controlled electrically, rather than purely geometrically.

The choice of different materials for the electrode layers 12, 16 of the nanoresonator plays an important part in the process of manufacturing the nanoresonator, as will be made clear by the remainder of this description, since it allows the nanoresonator structure to be separated, in a process of lithographic definition of the structure of the device, from a sacrificial forming substrate on which it is deposited and configured in a predetermined designed layout.

The prismatic structure of the nanoresonator 10 has layers 12, 14 and 16 which are freely accessible and can be functionalized independently of each other, since they have at least one surface area, 12', 14' and 16' respectively, exposed to the environment. In the case considered by way of example, the surface areas 12', 14' and 16' exposed to the environment coincide with at least the side surface of each layer, while the lower and upper bases 12", 16", respectively, of the electrode layers at the ends of the stack can also be exposed to the environment.

The equivalent electrical circuit of the exemplary nanoresonator structure according to the invention is shown next to the three-dimensional representation of said structure. It consists of an LC resonant circuit, in which the inductive behaviour is determined by the antiparallel loop current propagated in the pair formed by the electrode layers, and the outer regions of the electrode layers, where the current causes an accumulation of opposing charges, act as the plates of a capacitor.

By way of example, a nanoresonator structure adapted to resonate in the near infrared range has dimensions of about 200 nm on its long side and 100 nm on its short side, and each layer has a thickness of 50 nm, making the nanoresonator arranged for use in biological applications. On the other hand, a nanoresonator adapted to resonate in the THz range has typical dimensions between 2 μm and 10 μm.

Figure 2B:
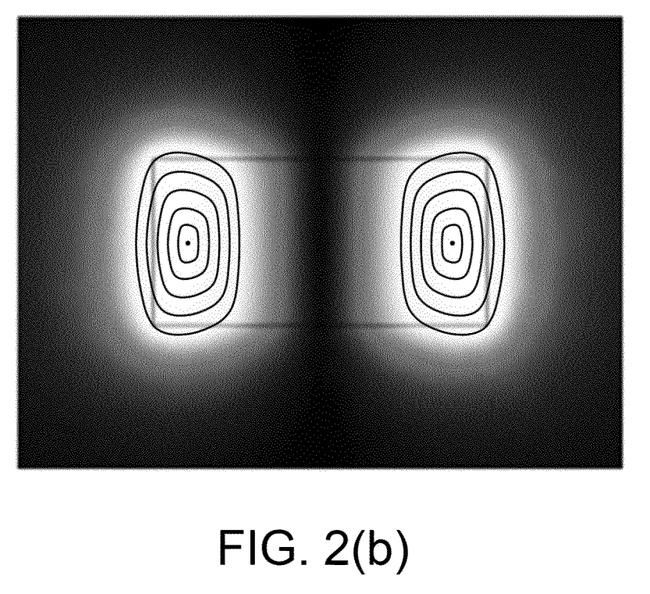
Figure 2C:
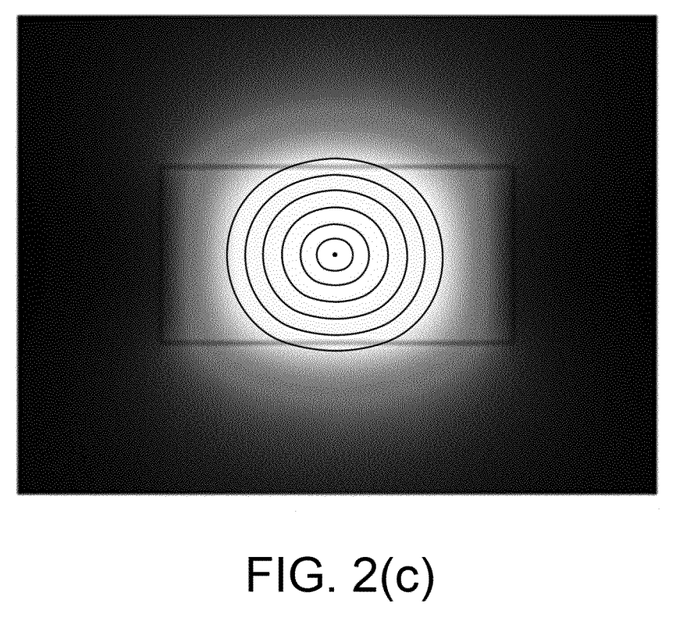

FIG. 2b shows the pattern of the lines of electric field intensity established on the nanoresonator, and FIG. 2c shows the intensity pattern of the magnetic field lines established on the nanoresonator. The electric field is confined to the sides, at the smaller faces of the structure, while the magnetic field is concentrated around the central region of the structure; that is to say, the two ends of the nanoresonator exhibit capacitive behaviour and the central portion of the structure exhibits inductive behaviour.

The steps of a process for the manufacture of nanoresonators 10 proposed by the invention are described with reference to FIGS. 3a-3h.

The manufacturing process, which is itself inventive, includes three different macro steps, namely the manufacture of an array of nanoresonators on a supporting substrate by planar lithography, the separation of the nanoresonators from the substrate and the conjugation of the nanoresonators once they are free, in other words no longer rigidly fixed to the substrate, with chemical agents adapted to facilitate the formation of a stable colloidal suspension in a liquid medium.

Figure 3A:
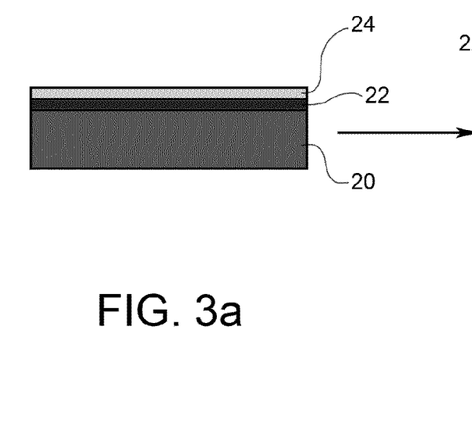
FIGS. 3a-3h show a succession of steps of a process for manufacturing a set of nanoresonators proposed by the invention, by means of lithography, dry etching, wet etching, and chemical functionalization.

With reference to FIG. 3a, this shows a gallium arsenide substrate 20 adapted to support the formation of an array of resonant nanostructures, on which a first conductive layer 22 of aluminium is deposited, by evaporation for example, so as to form a first electrode 12, and an intermediate layer 24 of aluminium oxide ($Al_2O_3$) is also deposited, by known sputtering techniques for example, so as to form an intermediate dielectric 14 of the nanoresonator structure of FIG. 2a.

Figure 3B:
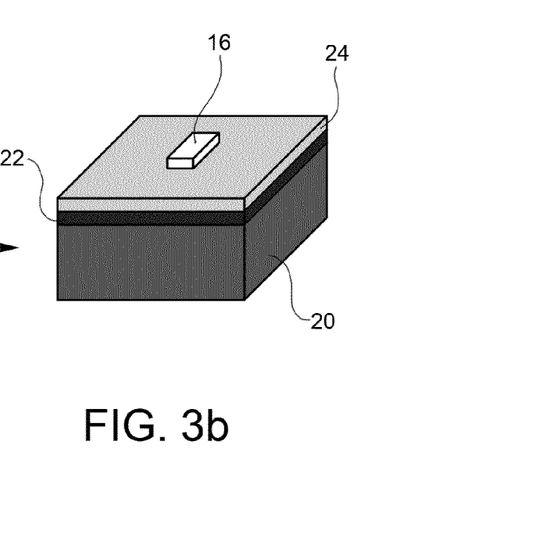

FIG. 3b shows a subsequent step of lithography which is carried out by using an electronic beam to expose a commercial positive resist (ARP 67902), previously deposited by spin coating at 400 r.p.m. and baked at 170° C. for 5 minutes. When the resist has been exposed and developed, a second conductive layer of gold is deposited, so as to form a second electrode 16 of the nanoresonator structure. In order to improve the adhesion to the aluminium oxide layer, the evaporation of the gold is preceded by the deposition of a thin layer of chromium (5 nm). Additionally, the deposition of the gold is followed by the evaporation of a layer of nickel (10 nm) which is used as a mask for the dry etching. This is followed by a lift-off for 24 hours (in acetone) to remove the unexposed resist and the metal deposited thereon, so as to provide a pattern configuration in which individual pads corresponding to the electrode 16 of the nanoresonator structure appear on the layering of aluminium and native oxide.

Figure 3C:
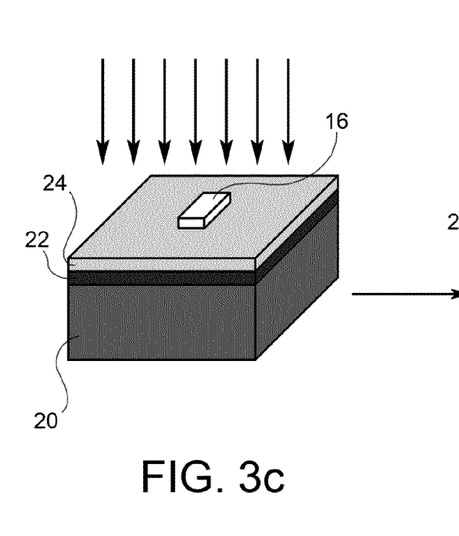

As shown in FIG. 3c, a dry etching step is then performed, using a technique of reactive ion etching through a reactive plasma (inductively coupled plasma) of $BCl_3$, $Cl_2$ and Ar, to remove the first conductive layer of aluminium (layer 22) and the intermediate layer of aluminium oxide (layer 24) located thereon, with the use of the masking provided by the gold electrode pads 16; in other words, the removal takes place in the regions outside the stacked configuration of the nanoresonator structure.

Figure 3D:
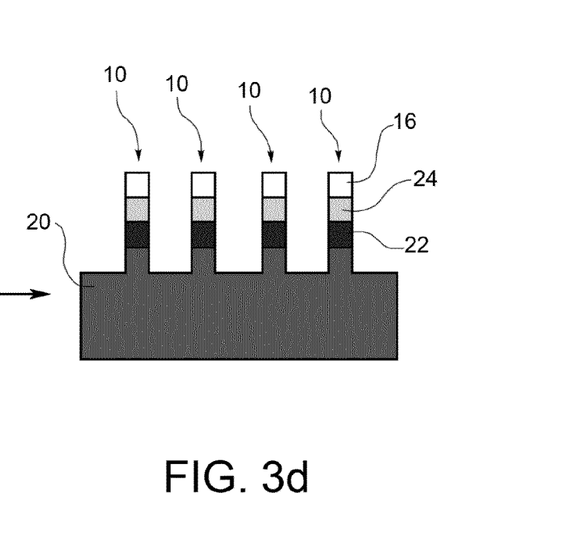

Thus an array of independent nanoresonator structures, organized in a stable way on the substrate 20, is obtained as shown in FIG. 3d.

Figure 4A:
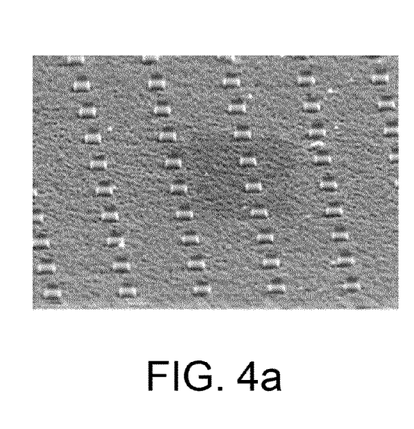
FIGS. 4a and 4b are, respectively, overall and enlarged electron microscope views of an ordered array of nanoresonators produced in a first step of the manufacturing process according to the invention.
Figure 4B:
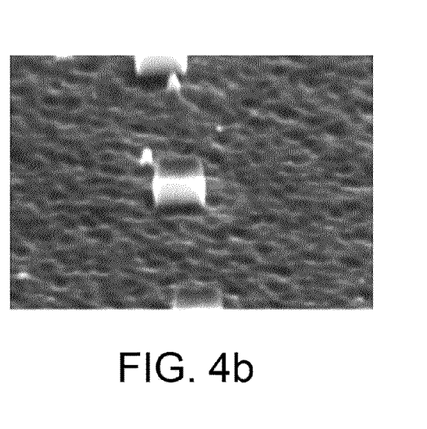

FIG. 4a shows a scanning electron microscope image of a regular array of nanoresonators fixed to a GaAs substrate, the nanoresonators being spaced one micron apart in both directions on the plane. FIG. 4b shows an enlarged view of the image of FIG. 4a.

Figure 3E:
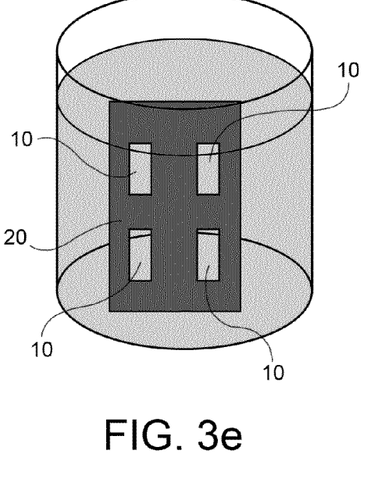
Figure 3F:
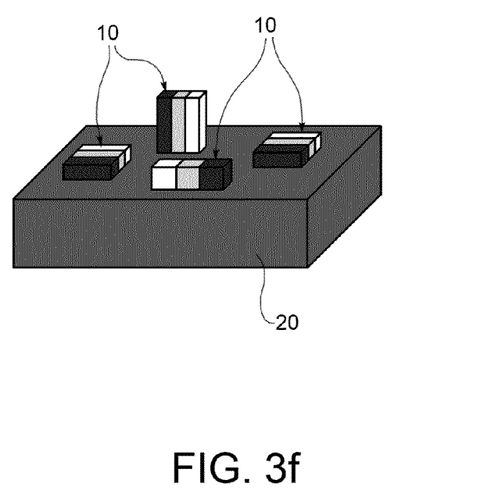

After the array of nanoresonator structures has been formed on a substrate, they are removed from the substrate as shown in FIG. 3e. In this step, a method of wet etching is adopted, using acetic acid and hydrogen peroxide. The preferred concentration for the solution is: $C_2H_4O_2$:$H_2O$:$H_2O_2$=20 µl: 6 ml: 2 ml, and the specimen is held in solution for about five hours.

Figure 4C:
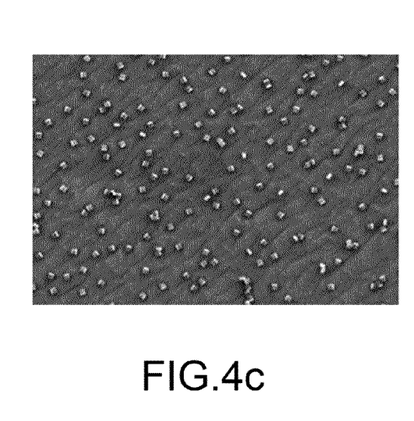
FIGS. 4c and 4d are, respectively, overall and enlarged microscope views of a collection of dispersed nanoresonators produced in a second step of the manufacturing process according to the invention, after the process of detachment of the nanoresonators from the substrate.
Figure 4D:
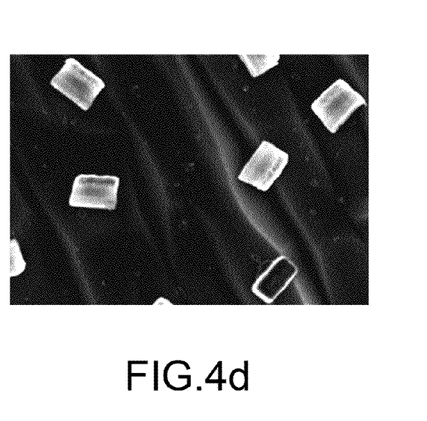

After this treatment, the nanoresonator structures are released from the substrate, although they continue to adhere weakly to it because of adhesion forces such as the Van der Waals force, in random positions, being tipped onto one side or inverted, for example. The result of this step is shown schematically in FIG. 3f, where the solution (water, for example) has been removed under a vacuum, and scanning microscope images are reproduced in FIGS. 4c and 4d, showing an overall view and an enlarged view respectively.

Figure 3G:
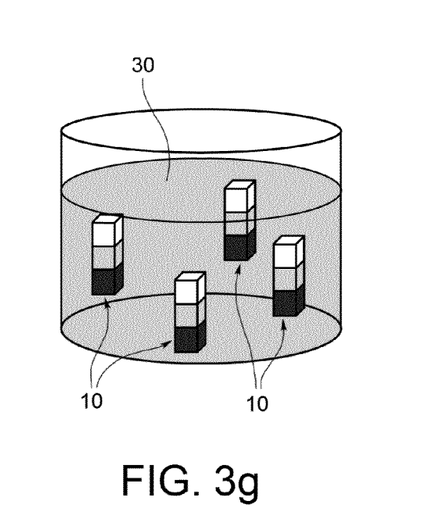

As shown in FIG. 3g, the nanoresonator structures, which are now released from the substrate and are independent of each other, are then dispersed in a liquid medium 30. This process is facilitated by a fast sonication step (for 40 seconds) in a vessel containing N,N-dimethylformamide (DMF).

In order to obtain the most uniform possible dispersion of the nanostructures in a liquid medium, for example water, and to prevent their aggregation and precipitation, the resonant nanostructures are preferably coated with an alkoxysilane such as APTES ((3-aminopropyl-triethoxysilane) modified with a polyethylene glycol (PEG) chain (MW=550 Da), by means of the amine group, to improve the stability and biocompatibility of the suspension.

Figure 3H:
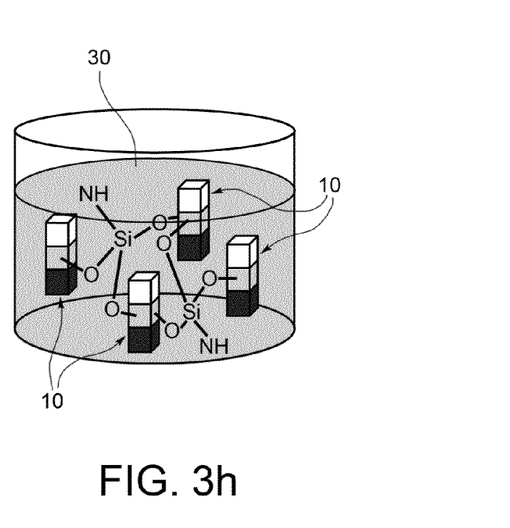

As shown in FIG. 3h, the nanoresonators are functionalized with APTES, which contributes ethoxysilane groups that react with hydroxylated surfaces such as the Al and $Al_2O_3$ surfaces, causing the formation of Si—O-surface bonds with the exposed surface 14' of the intermediate layer 14 of dielectric material and with the exposed surfaces 12' and 12" of the first electrode layer 12 of conductive material. Since the surface of the second electrode layer 16 of gold, exposed to the environment, has no hydroxyl groups, only the exposed areas of the intermediate dielectric layer 14 of aluminium oxide and of the first electrode layer 12 of aluminium are functionalized.

The reaction takes place when the nanoresonators are in suspension in N,N-dimethylformamide, after the sonication step described with reference to FIG. 3g, after the addition of APTES modified with polyethylene glycol and acetic acid, which act as catalysts, at a reflux temperature for a period of 24 hours.

After the removal of the solvent under a vacuum, the nanostructures functionalized in this way can be dispersed in water by sonication and purified by dialysis through a membrane, preferably with a cut-off of 10 kDa.

The properties of resonance in the optical range of specimens of nanoresonators as proposed by the invention and manufactured by the inventors according to the inventive method were measured with a Nexus Fourier transform spectrometer fitted with a white light lamp and a lead selenide detector. Measurements of reflectance were made on an array of nanoresonators fixed to the manufacturing substrate, and on a collection of nanoresonators which were no longer fixed to the substrate in an ordered array, but had adhered to it in random positions and orientations.

Figure 5A:
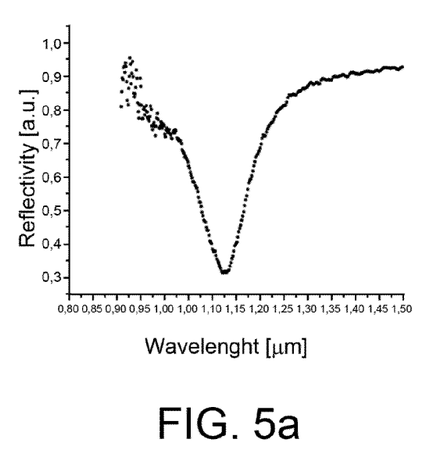
FIGS. 5a and 5b are diagrams showing the resonance properties (in the optical range) of the nanoresonators proposed by the invention.
Figure 5B:
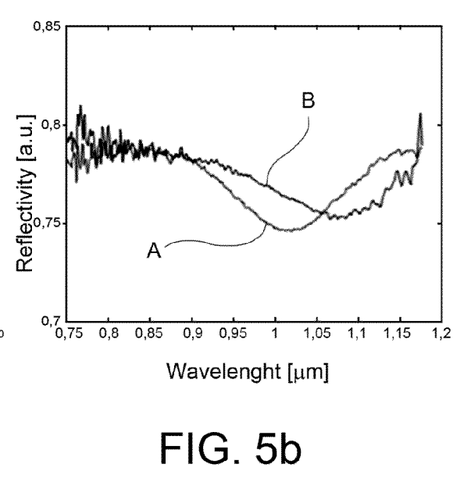

FIG. 5a shows the result of the reflectance measurements for an array of nanoresonators on a substrate (as in FIG. 4a), and FIG. 5b shows the results of the reflectance measurements for a collection of nanoresonators adhering to the substrate (as in FIG. 4b), in a condition of exposure to air (curve A) and in a condition of exposure to water (curve B) respectively.

The resonance spectrum was calculated as the ratio between the spectrum of the nanoresonators and the spectrum of the substrate only.

FIG. 5b shows a measurable shift in the resonant frequency as a result of the different dielectric properties of the medium (air or water) in which the nanoresonators are immersed, which affects the determination of the overall capacitance viewed from the structure and ultimately affects the resonant frequency.

A second set of experiments was conducted using a microfluidics device to make accurate measurements of the behaviour of the nanoresonators when immersed in a liquid environment. In a test chamber having dimensions of about 200× 200×30 µm, illuminated with a beam of light focused on a diameter in the range from 30 µm to 100 µm, the transmission spectra of the nanoresonators proposed by the invention were acquired in different conditions of immersion in the environment, that is to say in different dispersion environments of the nanoresonators.

Figure 6:
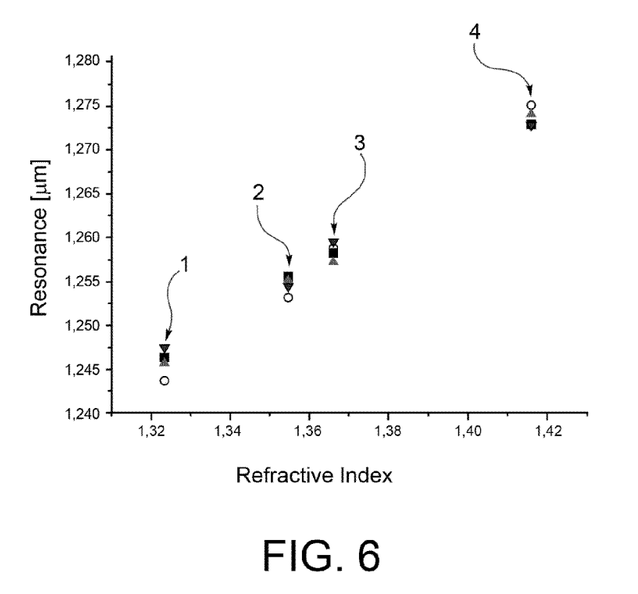
FIG. 6 is a diagram showing the resonance properties (in the optical range) of the nanoresonators proposed by the invention immersed in a fluid medium.

Different liquids, namely water, ethanol, isopropanol and PDMS (polydimethylsiloxane) respectively, characterized by different refractive indices, were introduced into the microfluidics chamber in sequence. FIG. 6 shows the dependence of the resonance wavelength on the refractive index of the medium in which the nanoresonators are dispersed; that is to say, ultimately, the liquid medium in which the nanoresonators are immersed. Four sets of reproducibility measurements are reported for each environment, indicated by the references 1, 2, 3 and 4 respectively, for water, ethanol, isopropanol and PDMS. These measurements demonstrate a linear dependence of the resonance on the refractive index of the liquid in which the nanoresonators are immersed. Overall, the result demonstrates the sensitivity of the nanoresonators proposed by the invention to the physical and chemical dispersion environment.

The inventors have also investigated the effects of the chemical bonds on the metallic surfaces of the nanoresonators (electrodes 12 and 16), by progressively exposing the nanoresonators to a solution of cysteamine diluted 1:1000 in water. It is known that cysteamine forms bonds with gold, in this case with the electrode 16 of the nanoresonator, forming a sulphur bridge and thereby affecting the optical properties of the nanoresonator.

Figure 7:
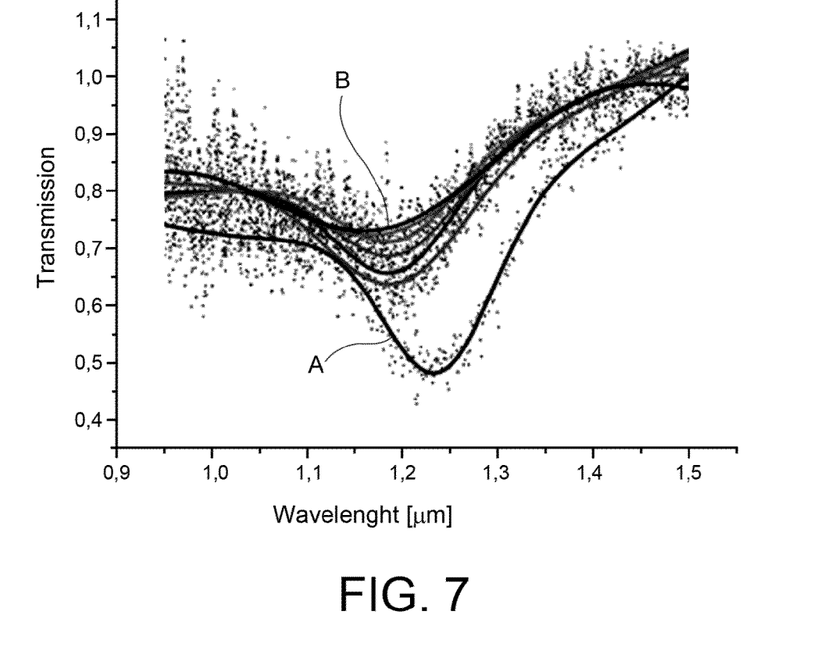
FIG. 7 is a diagram showing the resonance properties (in the optical range) of the nanoresonators proposed by the invention as a function of the bond with an analyte in a molecular sensing application.

FIG. 7 shows the time dependence of the optical transmission curves of the nanoresonators proposed by the invention in the presence of cysteamine. A shift in resonance wavelength of about 50 nm is observable between the condition in which the nanoresonators are free of bonds (the condition in which cysteamine is absent, shown by curve A) and the condition in which the nanoresonators are functionalized with bonds to cysteamine (after a period of 30 minutes of exposure to cysteamine in solution, shown by curve B). A gradual reduction of the amplitude of the transmission signal can also be observed, the time dependence of this signal being attributable to the kinetics of the cysteamine bonds.

The results of this experiment prove that the nanoresonators proposed by the invention can be used for making probes for molecular interactions with their surfaces exposed to the environment.

Advantageously, the structure of the nanoresonator proposed by the invention, which is completely free and detached from any substrate, has a plurality of areas exposed to the environment, these areas belonging to layers of different materials, allowing multiple functionalization of the nanoresonator (for what are known as multi-sensing applications).

Figure 8:
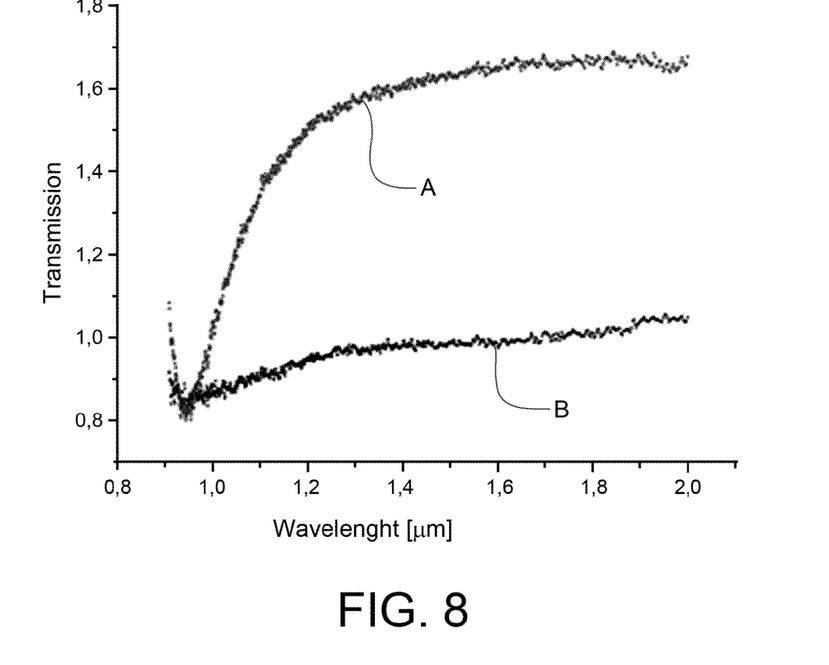
FIGS. 8 and 9 are diagrams showing the resonance properties (in the optical range) of the nanoresonators proposed by the invention dispersed in solution in a liquid.

FIG. 8 shows the optical response of the nanoresonators proposed by the invention dispersed in a liquid medium, specifically a suspension in water of nanoresonators coated with APTES modified with PEG, prepared as described with reference to FIGS. 3a-3h. This figure shows the transmission spectrum as a function of the wavelength, which shows a strong resonance peak at the 0.95 µm wavelength (curve A) by comparison with the transmission spectrum of water (curve B), demonstrating that the optical response of the nanoresonators proposed by the invention is detectable in dispersion in a liquid phase, even for very small numbers of sensors. This is because the nanoresonators proposed by the invention have a much higher sensitivity than the prior art nanoparticles.

Figure 9:
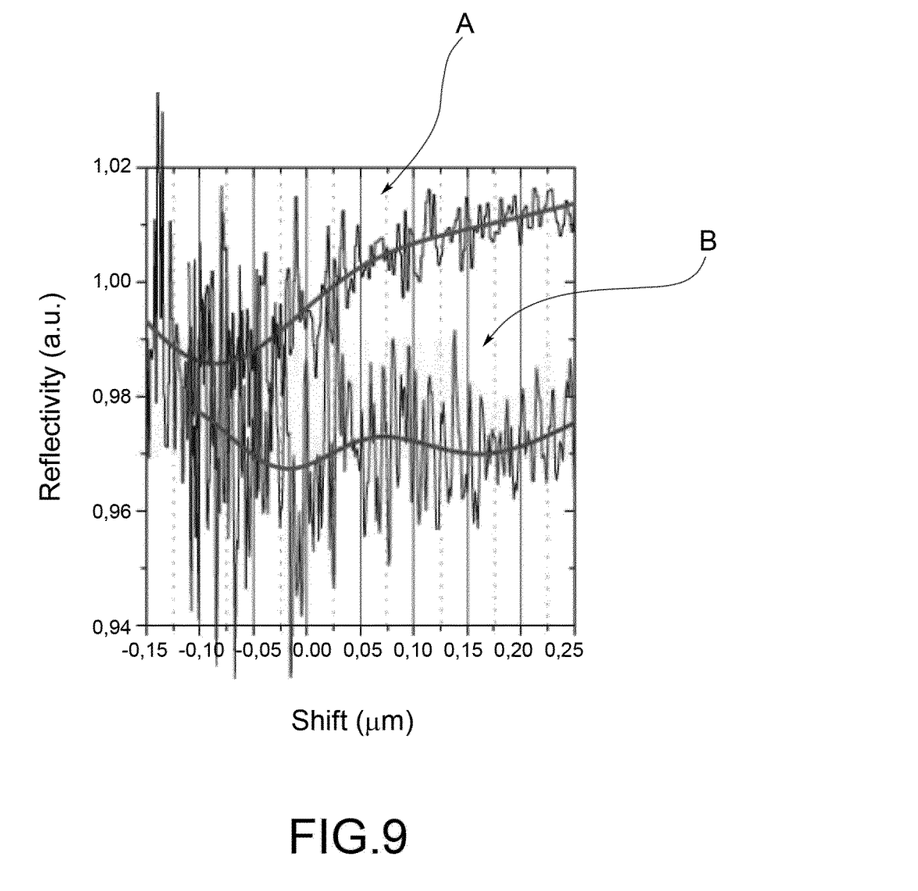

FIG. 9 shows the spectra of nanoresonators dispersed in two different solvents, namely water (curve A) and DMSO (curve B) respectively, characterized by different refractive indices. An interpolation curve is provided for each spectral pattern. The horizontal axis of the graph shows a shift relative to the resonance of the respective nanoresonators when fixed to the substrate and exposed to air. In both cases, a blue shift of the resonance is observable by comparison with the measurement made on an array of nanoresonators fixed to a substrate, where the high refractive index of the gallium arsenide substrate is dominant. The ratio between the shifts of resonance in the solutions in water and DMSO is 4.25. The resonance contrast is approximately 1%, a factor 20 times smaller than in the case of nanoresonators fixed to the substrate, consistent with the random orientation of the nanoresonators in liquid suspension, and with the resonance damping due to the molecular bond of the APTES. These findings demonstrate the sensitivity of the resonant nanostructures according to the invention in the condition of immersion in a solvent, and the difference in spectra as a function of the solvent used provides qualitative proof of the efficacy of detection applications in the liquid phase using the nanoresonators proposed by the invention.

In conclusion, the results of the experiments demonstrate that the three-dimensional structured nanoresonators proposed by the invention, produced by lithography on a sacrificial substrate followed by separation of the structure from the substrate and suspension in a liquid medium, have optical properties of sensitivity to the physical and chemical dispersion microenvironment, and to any chemical bonds formed by functionalization, and are therefore promising devices for use as nanosensors in a wide range of applications.

It has also been demonstrated that these nanoresonators can be detected optically in a stable liquid dispersion, a feature which has proved to be essential for use in injections into living organisms, for the study of absorption in porous media, and for microfluidics assaying.

It should be noted that the proposed embodiment of the present invention in the preceding discussion is described purely by way of example and does not limit the present invention. A person skilled in the art can easily apply the present invention in different embodiments which do not depart from the principles described above, and which are therefore included in the present patent.

This is true, in particular, as regards the possibility of using lithographic techniques other than electron beam lithography, for example nanoimprint lithography, for defining the three-dimensional structure of the nanoresonators.

Nanoimprint lithography can be used to obtain a greater number of nanoresonators, up to $10^6$-$10^9$ nanoresonators in each process, thus reducing the process time. This is because a single pass in electronic beam lithography has a typical duration of twelve hours, whereas the typical duration of a nanoimprint lithography process is reduced to a few minutes.

The surfaces of the nanoresonators proposed by the invention can also be conjugated with molecular groups which promote specific transport mechanisms, for example peptides for cell penetration which may facilitate the internalization of the device in living cells, or which promote the bonding and accumulation of the nanoresonators in certain tissues or cell types.

The properties of the nanoresonators proposed by the invention, demonstrated by the experimental results discussed above, make it possible to use these nanoresonators advantageously as contrast media in a wide variety of biological and medical applications. For example, a dispersion of nanoresonators in a liquid medium, where the nanoresonators are designed to resonate in a region of the electromagnetic spectrum in which absorption by cells and tissues is fairly low, can be used as a contrast medium for medical imaging. The inventors expect that the use of the nanoresonators proposed by the invention will be able to improve the characterization of tissues and the diagnosis of numerous diseases, including cancers.

The detection capacity of nanoresonators can also be used to detect molecular interactions in vivo or in biological assays, for example in order to monitor gene expression, to detect proteins or enzymes in tissues and cells, or for toxicological purposes. The size of a nanoresonator proposed by the invention is rather smaller than the size of a cell, making it possible to use the nanoresonators as intracellular probes. The internalization of the nanoresonators is possible because of their nanometric size and can be promoted by functionalization with peptides adapted to penetrate the cell membranes or other molecular groups.

The nanoresonators proposed by the invention can also be used for environmental applications, for example in the detection of pollutants or for the study of porous materials which can be impregnated with liquid suspensions containing a set of dispersed nanoresonators.

Provided that the principle of the invention remains the same, the forms of embodiment and details of construction may be varied widely with respect to those described and illustrated, which have been given purely by way of non-limiting example, without thereby departing from the scope of protection of the present invention as defined by the attached claims.

The invention claimed is:

1. Three-dimensional electromagnetic nanoresonator structure, comprising a stack of laterally confined layers including at least a first layer and a second layer of a respective conductive material between which a dielectric layer is interposed, which can be represented by a resonant equivalent electrical circuit having a nominal resonant frequency determined by geometrical dimensions of the structure,
   wherein said first and second layer include different conductive materials, and
   said layers of conductive material and said dielectric layer have at least a respective accessible surface area, adapted to be exposed in a liquid environment in which said structure is immersed.

2. Structure according to claim 1, comprising a prismatic shape in which said layers of conductive material have an accessible base surface and an accessible side surface, and said dielectric layer has an accessible side surface.

3. Structure according to claim 1, wherein said first layer of conductive material is made of aluminium, said dielectric layer is made of aluminium oxide and said second layer of a conductive material is made of gold.

4. Structure according to claim 1, comprising a nominal resonant frequency in the infrared spectral region.

5. Method for manufacture of three-dimensional nanoresonators dispersible in a liquid medium, comprising the steps of:

forming an array of electromagnetic nanoresonators anchored to a sacrificial supporting substrate, the array including a plurality of independent three-dimensional electromagnetic nanoresonator structures, each of the nanoresonator structures comprising at least a first layer and a second layer of a respective conductive material between which a dielectric layer is interposed, each structure being representable by a resonant equivalent electric circuit having a nominal resonant frequency determined by the geometrical dimensions of the structure, each of said layers having at least a respective accessible surface area, adapted to be exposed in a liquid environment in which said structure is immersed, wherein said first layer and said second layer include different conductive materials;

separating said nanoresonators from the substrate; and conjugating an accessible surface area of at least a layer of each nanoresonator structure with a chemical agent adapted to facilitate formation of a stable colloidal suspension of said nanoresonator structures in a liquid medium.

6. Method according to claim 5, in which forming an array of nanoresonators includes the steps of:

providing a gallium arsenide sacrificial substrate adapted to support formation of said array of nanoresonators, and in succession thereon:

depositing a first layer of electrically conductive material;

depositing on said first layer of electrically conductive material an intermediate layer of dielectric material;

depositing on said layer of dielectric material a second layer of electrically conductive material different from the material forming said first layer, according to a predetermined configuration of the array of nanoresonators defined by lithography; and selectively removing said first layer of electrically conductive material and said intermediate layer of dielectric material from regions on the substrate that are external to the configuration of said array of nanoresonators, so as to obtain a plurality of independent stacked nanoresonator structures.

7. Method according to claim 6, wherein said first layer of conductive material is made of aluminium, said dielectric layer is made of aluminium oxide and said second layer of conductive material is made of gold.

8. Method according to claim 6, wherein said selective removal takes place by dry etching, using a reactive plasma of $BCl_3$, $Cl_2$ and Ar.

9. Method according to claim 5, wherein the separation of the nanoresonators from the substrate comprises wet etching with acetic acid and hydrogen peroxide.

10. Method according to claim 5, including dispersion of the independent nanoresonator structures, separated from the substrate, in a liquid medium by sonication in N, N-dimethylformamide.

11. Method according to claim 5, comprising conjugating said nanoresonator structures with an alkoxysilane compound, by Si—O group bonds with an accessible surface area of at least one layer of the structure which has hydroxyl groups.

12. Method according to claim 11, comprising conjugating said nanoresonator structures with APTES, 3-aminopropyl-triethoxysilane, modified with polyethylene glycol.

13. Method according to claim 5, comprising conjugating at least an accessible surface area of a layer of said nanoresonator structures with molecular groups which promote transport mechanisms.

14. Method according to claim 13, wherein said molecular groups which promote transport mechanisms include peptides adapted to penetrate a cell membrane.

15. Method according to claim 5, comprising conjugating at least an accessible surface area of a layer of said nanoresonator structures with molecular groups which promote bonds with a living tissue, or with a cell or with a chemical substance.

* * * * *